United States Patent [19]

Goettsche et al.

[11] Patent Number: 5,179,116

[45] Date of Patent: Jan. 12, 1993

[54] WOOD PRESERVATIVES

[75] Inventors: Reimer Goettsche; Hans-Volker Borck, both of Baden-Baden; Hans-Norbert Marx, Buehl-Vimbuch, all of Fed. Rep. of Germany

[73] Assignee: Dr. Wolman GmbH, Sinzheim, Fed. Rep. of Germany

[21] Appl. No.: 895,421

[22] Filed: Jun. 5, 1992

Related U.S. Application Data

[63] Continuation of Ser. No. 638,005, Jan. 4, 1991, abandoned, which is a continuation of Ser. No. 263,375, Oct. 27, 1988, abandoned.

[30] Foreign Application Priority Data

Oct. 27, 1987 [DE] Fed. Rep. of Germany ....... 3736298

[51] Int. Cl.⁵ .................... A01N 33/02; A01N 37/30; A01N 43/52
[52] U.S. Cl. .................................. 514/388; 514/554; 514/563; 514/663
[58] Field of Search ................ 514/388, 554, 563, 663

[56] References Cited

U.S. PATENT DOCUMENTS 4,567,277  1/1986  Marx et al. .......................... 514/388

FOREIGN PATENT DOCUMENTS 585129  2/1987  Australia .
589262  4/1987  Australia .
0234462  2/1987  European Pat. Off. .
0242753  10/1987  European Pat. Off. .
2151229  7/1988  United Kingdom .

*Primary Examiner*—Allen J. Robinson
*Attorney, Agent, or Firm*—Oblon, Spivak, McClelland, Maier & Neustadt

[57] ABSTRACT

A wood preservative which is based on a dimethylalkylamine and an acid and contains dimethylalkylamine, a water-soluble acid and a water-insoluble acid and/or 2-(methoxycarbonylamino)-benzimidazole is used for preserving wood.

6 Claims, No Drawings

WOOD PRESERVATIVES

This application is a continuation of application Ser. No. 07/638,005, filed on Jan. 4, 1991, which is a continuation of application Ser. No. 07/263,375, filed on Oct. 27, 1988, now both abandoned.

The present invention relates to water-soluble wood preservatives for preserving, in particular, fresh wood, for example freshly cut wood in sawmills or freshly felled timber in the forest.

It is known that dimethylalkylamines, 2-(methoxycarbonylamino)-benzimidazole (BCM) or N-tridecyl-2,6-dimethylmorpholine (tridemorph), for example in the form of their salts, can be used for preserving wood (EP-147 976, DE-3 138 575.3 and DE-3 507 420.5). However, their actions are unsatisfactory.

We have found that wood preservatives which contain a) a dimethylalkylamine, b) a water-soluble acid and c) a water-insoluble acid or BCM or c) a water-insoluble acid and 2-(methoxycarbonylamino)-benzimidazole have a very good action against wood pests, in particular fungi, the action being better than that of the known wood preservatives. The novel wood preservatives are water-soluble. They are used in the form of aqueous impregnating solutions, which are prepared from the wood preservatives (concentrates) by dilution with water. The present invention relates both to the concentrates and to the dilute aqueous solutions (impregnating solutions) obtainable by diluting the concentrates with water. The novel wood preservatives are suitable for protecting wood, in particular fresh wood, as obtained, for example, as freshly cut wood in sawmills or as freshly felled timber in the forest.

A dimethylalkylamine is an N,N-dimethyl-N-alkylamine where alkyl is, for example, of 6 to 20, preferably 12 to 14, carbon atoms. In addition to the pure dimethylalkylamines, it is also possible to use mixtures, for example mixtures of dimethyl-C12-alkylamine and dimethyl-C14-alkylamine (dimethyl-$C_{12}/C_{14}$-alkylamine).

A water-soluble acid is, for example, a water-soluble inorganic acid, for example an acid of phosphorus, in particular phosphonic acid ($H_3PO_3$), phosphinic acid ($H_3PO_2$), acidic phosphoric esters (e.g. mono- or dialkyl phosphate, for example monobutyl phosphate or dibutyl phosphate) or monoalkyl phosphonates, or an acid of sulfur, e.g. a sulfonic acid, for example benzenemonosulfonic or benzenedisulfonic acid, sulfamic acid or 4-phenolsulfonic acid, or an organic $C_2-C_4$-carboxylic acid, for example a monocarboxylic acid, e.g. acetic acid, propionic acid, methoxyacetic acid, lactic acid or glycollic acid, or polycarboxylic acids, e.g. fumaric acid, citric acid or maleic acid.

A water-insoluble acid is, for example, an aliphatic $C_5-C_{20}$-carboxylic acid, for example a monocarboxylic acid, such as hexanoic acid, heptanoic acid, octanoic acid, nonanoic acid, decanoic acid, 2-ethylpentanoic acid, 2-ethylhexanoic acid, 2-ethylheptanoic acid, isooctanoic acid, isononanoic acid or versatic acids (highly branched monocarboxylic acids), or a dicarboxylic acid, e.g. decanedicarboxylic acid.

The acids can also be used in the form of their salts, e.g. dimethylalkylamine salts. The BCM-containing agents may also contain a water-insoluble acid, in addition to the water-soluble acid.

The wood preservatives are water-miscible, form clear solutions with water and, in the usual concentration for use (from 0.5 to 0.0% by weight, based on the concentrate), have a pH of less than 7.0 when a dimethylalkylamine is used exclusively, a pH of less than 6 when mixtures of a dimethylalkylamine with tridemorph are used and a pH of less than 3.5 when mixtures of dimethylalkylamine with BCM are used. They are prepared by mixing the individual components with one another.

The wood preservatives (concentrates) are more or less viscous solutions whose viscosity can be reduced by adding polar solvents. Examples of suitable polar solvents are dimethylformamide, diethylformamide, N-methylpyrrolidone, dimethyl sulfoxide, glycols, polyglycols, glycol ethers, glycol ether acetates and alcohols. In these cases, the BCM salt is generally in pasty form.

The concentrates generally contain
from 5.0 to 75.0, in particular from 30 to 50, % by weight of a dimethyl-$C_6-C_{20}$-alkylamine,
from 0 to 75.0, in particular from 15 to 25, % by weight of tridemorph,
from 0 to 25.0, in particular from 4 to 12, % by weight of BCM,
from 2.5 to 50.0, in particular from 10 to 45, % by weight of a water-soluble acid,
from 0 to 25.0, in particular from 5 to 15, % by weight of a water-insoluble acid and
from 0 to 50.0, in particular from 4 to 30, % by weight of a solvent, the sum being 100% by weight in each case. The mixing ratio (parts by weight) of BCM to dimethylalkylamine is, for example, from 1 : 50 to 2 : 1, preferably from 1 : 20 to 1 : 2.

Water, which, for example, is present in the commercial form of the acids, may also be present.

The following may additionally be used: wetting agents, corrosion inhibitors, colorants and, if required, binders.

In order to improve the range of action of the wood preservatives, they may additionally contain nitrogen-containing organic fungicides, for example further morpholine derivatives, e.g. fenpropemorph or aldimorph, guanidine derivatives, e.g. dodecylguanidine, chlorhexadine or guazatine, imidazole derivatives, e.g. imazalil, dodecylimidazole or glyodine, pyrimidine derivatives, e.g. hexatidine, or quaternary ammonium compounds, e.g. N-dodecylpyridinium chloride. Other fungicides may also be used, for example 2-(thiocyanomethylthio)-benzothiazole, 3-iodo-2-propynylbutyl carbamate, 2-(4-thiazolyl)-benzimidazole or water-soluble salts (e.g. the potassium salt) of N-cyclohexyldiazenium dioxide.

Other fungicides too, such as furmecyclox or benodanil, or insecticides, such as lindane or permethrin, can be added to the formulations and should be incorporated with or without the addition of emulsifiers, for example oxyethylated nonylphenols.

Depending on the danger to which the wood is exposed, application for preservation of the wood may be effected, for example,
a) by spraying the wood with the solution,
b) by dipping the wood into the solution,
c) by impregnating the wood by means of pressure differences, for example by the pressure process or double vacuum impregnation, or
d) by spreading the preservative over the wood.

In the case of secondary wood products, for example cut wood and pulp, and other industrial products or cellulose-containing materials which are susceptible to fungal attack, for example intermediates in papermaking, ligneous annual plants (bagasse, rape), the application should be adapted to the technical possibilities.

The wood-preserving activity of the agents covers, for example, a) molds (e.g. *Aspergillus niger*),
b) fungi which cause wood rot (e.g. *Chaetomium globosum*),
c) blue stain fungi (e.g. *Pullularia pullulans*) and
d) wood-destroying Basidiomycetes (e.g. *Serpula lacrymans*);

in particular, the action against blue stain fungi is very good.

The wood preservatives have a very good fungicidal action, as shown by the experiments below.

The experiments were carried out using fresh, sawn pine sapwood timbers measuring 200×50×15 mm, which had been deep-frozen at the beginning of the experiment.

After thawing out (which takes about 6 hours), the timbers were dipped for about 10 seconds in the solutions to be applied, placed in an inclined position to drip off, stored under a roof for about 24 hours under normal atmospheric conditions and then placed in the test area. Ten sample boards were impregnated with each individual test solution in the manner described above. Unimpregnated control timbers were dipped into pure water.

The test area chosen was a shady meadow, whose grass was cut short before the test timbers were laid out. The test timbers were placed on two plastic rails, at a height of about 1 cm above the grass.

The test boards exposed to outdoor weather (rain) were checked after two months (August/September).

The fungicidal activity was classified in four categories on the basis of the resulting discoloration and changes in the wood surface:

O: No overgrowth
+: Slight spot-like superficial overgrowth
++: More extensive spot-like overgrowth
+++: Large areas of overgrowth or completely overgrown.

COMPARATIVE EXAMPLE 50.00% of dimethyl-$C_{12}/C_{14}$-alkylamine
17.50% of phosphonic acid
22.50% of propylene glycol

| Concentration used | Appearance of the 10 test timbers |
|---|---|
| 2.5% | +++ |
| 5.0% | +++ |

COMPARATIVE EXAMPLE 50.00% of tridemorph
30.00% of phosphonic acid
20.00% of propylene glycol

| Concentration used | Appearance of the 10 test timbers |
|---|---|
| 2.5% | +++ |
| 5.0% | +++ |

EXAMPLE 1 (according to the invention)

50.00% of dimethyl-$C_{12}/C_{14}$-alkylamine
10.00% of 2-ethylhexanoic acid
15.00% of phosphonic acid
25.00% of propylene glycol

| | Appearance of the 10 test timbers | |
|---|---|---|
| Board No. | 2.5% use concentration | 5% use concentration |
| 1 | + | 0 |
| 2 | ++ | 0 |
| 3 | + | 0 |
| 4 | ++ | + |
| 5 | 0 | + |
| 6 | 0 | + |
| 7 | + | + |
| 8 | + | ++ |
| 9 | + | 0 |
| 10 | + | 0 |

EXAMPLE 2

30.00% of dimethyl-$C_{12}/C_{14}$-alkylamine
20.00% of tridemorph
25.00% of phosphonic acid
25.00% of propylene glycol

| | Appearance of the 10 test timbers | |
|---|---|---|
| Board No. | 2.5% use concentration | 5% use concentration |
| 1 | + | 0 |
| 2 | + | ++ |
| 3 | ++ | 0 |
| 4 | 0 | 0 |
| 5 | 0 | 0 |
| 6 | + | 0 |
| 7 | + | 0 |
| 8 | 0 | 0 |
| 9 | 0 | 0 |
| 10 | ++ | + |

EXAMPLE 3

35.00% of dimethyl-$C_{12}/C_{14}$-alkylamine
20.00% of tridemorph
10.00% of isooctanoic acid
35.00% of 85% strength lactic acid (15% of water)

| | Appearance of the 10 test timbers | |
|---|---|---|
| Board No. | 2.5% use concentration | 5% use concentration |
| 1 | + | + |
| 2 | 0 | + |
| 3 | ++ | + |
| 4 | 0 | 0 |
| 5 | + | 0 |
| 6 | + | + |
| 7 | + | + |
| 8 | + | 0 |
| 9 | + | + |
| 10 | ++ | 0 |

COMPARISON 25.00% of 2-(methoxycarbonylamino)-benzimidazole
37.50% of phosphonic acid
37.50% of water

| Concentration used | Appearance of the 10 test timbers |
|---|---|
| 0.25% | +++ |
| 0.50% | +++ |
| 1.00% | +++ |

EXAMPLE 4

30.00% of dimethyl-$C_{12}/C_{14}$-alkylamine
20.00% of tridemorph
10.00% of 2-ethylhexanoic acid
30.00% of phosphonic acid
5.00% of N-methylpyrrolidone
5.00% of 2-(methoxycarbonylamino)-benzimidazole

| Board No. | Appearance of the 10 test timbers Concentration used | | |
|---|---|---|---|
| | 2.0% | 3.0% | 4.0% |
| 1 | 0 | + | 0 |
| 2 | ++ | 0 | + |
| 3 | 0 | + | 0 |
| 4 | 0 | + | 0 |
| 5 | 0 | 0 | 0 |
| 6 | 0 | 0 | 0 |
| 7 | 0 | 0 | 0 |
| 8 | 0 | 0 | + |
| 9 | + | 0 | 0 |
| 10 | 0 | 0 | 0 |

COMPARATIVE EXAMPLE BCM 50.0% of 2-(methoxycarbonylamino)-benzimidazole
50% of sulfamic aid
(converted in a kneader under reduced pressure)

| Concentration used | Appearance of the ten test timbers after weathering |
|---|---|
| 0.25% | +++ |
| 0.50% | +++ |
| 1.00% | +++ |

EXAMPLE 5 (according to the invention)

47.5% of dimethyl-$C_{12}/C_{14}$-alkylamine
10.0% of 2-ethylhexanoic acid
30.0% of phosphonic acid
7.5% of N-methylpyrrolidone
5.0% of BCM

| Board No. | Appearance of the test timbers Concentration used | | |
|---|---|---|---|
| | 2.5% | 3.5% | 5.0% |
| 1 | + | + | + |
| 2 | + | + | 0 |
| 3 | ++ | + | + |
| 4 | 0 | ++ | 0 |
| 5 | 0 | 0 | + |
| 6 | ++ | + | 0 |
| 7 | 0 | + | + |
| 8 | + | + | 0 |
| 9 | ++ | + | 0 |
| 10 | 0 | + | + |

EXAMPLE 6

40.0% of dimethyl-$C_{12}/C_{14}$-alkylamine
40.0% of phosphonic acid
10.0% of N-methylpyrrolidone
10.0% of BCM

| Board No. | Appearance of the test timbers Concentration used | | |
|---|---|---|---|
| | 1.5% | 2.0% | 3.0% |
| 1 | + | + | + |
| 2 | ++ | + | + |
| 3 | + | + | 0 |
| 4 | ++ | 0 | + |
| 5 | + | ++ | 0 |
| 6 | + | + | + |
| 7 | + | 0 | + |
| 8 | + | ++ | + |
| 9 | + | + | 0 |
| 10 | ++ | + | + |

All test timbers which had not been treated were covered with blue stain fungi and were discolored (+++).

Another mixture having a good fungicidal action is the following:

35% of dimethyl-$C_{12}/C_{14}$-alkylamine
20% of tridemorph
10% of ethylhexanoic acid
30% of phosphonic acid
5% of N-methylpyrrolidone

We claim:

1. A wood preservative composition consisting essentially of:
   a) 30.0 to 50% by weight of an N,N-dimethyl-N-alkylamine where the alkyl group contains 6 to 20 carbon atoms;
   b) 5 to 15% by weight of a water-insoluble aliphatic carboxylic acid containing 5 to 20 carbon atoms or salt thereof;
   c) 2.5 to 45% by weight of a water-soluble acid selected from the group consisting of phosphonic, phosphinic, monoalkyl phosphate, dialkylphosphate, monoalkyl phosphonate, sulfamic, $C_2$–$C_4$ monocarboxylic, fumaric, citric and maleic;
   d) 0 to 25% by weight 2-(methoxycarboxylamino)-benzimidazole.

2. The wood preservative of claim 1 which has been diluted with a solvent to a concentration of 0.5% to 10.0% by weight.

3. The wood preservative of claim 1 wherein the water-soluble acid is phosphonic acid.

4. The wood preservative of claim 1 wherein the water-insoluble acid is 2-ethylhexanoic acid.

5. A process for preserving wood comprising applying an effective amount of the composition of claim 2 to wood.

6. A wood preservative composition consisting essentially of:
   a) 30.0 to 50% by weight of an N,N-dimethyl-N-alkylamine where the alkyl group contains 6 to 20 carbon atoms;
   b) 5 to 15% by weight of a water-insoluble aliphatic carboxylic acid containing 5 to 20 carbon atoms or salt thereof;
   c) 2.5 to 45% by weight of a water-soluble acid selected from the group consisting of phosphonic, phosphinic, monoalkyl phosphate, dialkylphosphate, monoalkyl phosphonate, sulfamic, $C_2$–$C_4$ monocarboxylic, fumaric, citric and maleic.

* * * * *